United States Patent [19]

Crozier et al.

[11] Patent Number: 5,165,901

[45] Date of Patent: Nov. 24, 1992

[54] PLATINUM GROUP METAL RECOVERY WITH A POLYAMINE

[75] Inventors: William D. Crozier, Westville, N.J.; Richard A. Grant, Caversham, United Kingdom

[73] Assignee: Johnson Matthey Public Limited Company, London, United Kingdom

[21] Appl. No.: 757,283

[22] Filed: Sep. 10, 1991

[30] Foreign Application Priority Data

Sep. 14, 1990 [GB] United Kingdom ............... 9020129

[51] Int. Cl.$^5$ .............................................. C01G 55/00
[52] U.S. Cl. .................................. 423/22; 423/213.5; 423/351; 75/720; 75/723
[58] Field of Search .............. 423/22, 351, 462, 213.5; 75/714, 723, 720; 210/682, 688; 556/136, 137

[56] References Cited

U.S. PATENT DOCUMENTS

| | | | |
|---|---|---|---|
| 3,960,549 | 6/1976 | MacGregor | 75/108 |
| 4,571,265 | 2/1986 | Konig et al. | 75/108 |
| 4,571,266 | 2/1986 | Konig et al. | 75/108 |
| 5,028,727 | 7/1991 | Verbeek et al. | 556/137 |
| 5,034,553 | 7/1991 | Verbeek et al. | 556/137 |

FOREIGN PATENT DOCUMENTS

| | | |
|---|---|---|
| 634425 | 1/1962 | Canada . |
| 2459098 | 6/1975 | Fed. Rep. of Germany . |
| 54-7256 | 4/1979 | Japan . |
| 1497534 | 1/1978 | United Kingdom . |

OTHER PUBLICATIONS

WO 82/00145, Platinum II Complexes & Antineoplastic Agents Containing Same as Effective Ingredients, (Abstract only), Jan. 21, 1982.

*Primary Examiner*—Theodore Morris
*Assistant Examiner*—Edward Squillante
*Attorney, Agent, or Firm*—Stevens, Davis, Miller & Mosher

[57] ABSTRACT

Rhodium and certain other PGM's in oxidation state III complex with chloride is precipitated from a solution by mixing with a polyamine, especially diethylene-triamine, in the presence of a protonating agent for the polyamine. High selectivity and high yields, in comparison to known reagents, are observed.

9 Claims, No Drawings

PLATINUM GROUP METAL RECOVERY WITH A POLYAMINE

This invention concerns improvements in refining, more especially it concerns improvements in the recovery of certain platinum group metals such as rhodium from solution.

It is known that platinum group metals ("PGM's") may be separated by solvent extraction and selective precipitation. Because of the similarity of the PGM's, this process is difficult and lengthy and has to be accomplished in a set order to avoid severe cross-contamination of the metals. The feedstock to such refining processes may be a feedstock derived from mining operations or from the recycling of PGM values, or a combination thereof, and may be contaminated with base metals and the other precious metals, gold and/or silver.

The metal rhodium is one of the most difficult to refine by separation from the other PGM's, and is usually the last metal to be recovered from a mixed PGM feedstock (see, for example, EP0049587A). Because of this, the relatively low availability of rhodium and the industrial demand, especially for automobile catalytic converters, rhodium is particularly expensive. It is desirable to devise a process which permits the recovery of rhodium from mixtures thereof with other PGM's and especially from mixtures with other PGM's and base metals and possibly other precious metals. Reference is made to The Pt Supplement Vol. A1 of Gmelin, published 1986, which suggests that the hexachloro complex $RhCl_6{}^{3-}$ can be precipitated in fairly selective manner, and that the use of ethylenediamine gives "very much better yields" than ammonia to precipitate the complex. We have studied ethylenediamine as a reagent for rhodium precipitation and concluded that the selectivity and yields were not adequate for a commercial scale operation.

The present invention provides a method for the precipitation of one or more of the platinum group metals rhodium, iridium, ruthenium and osmium from a feedstock solution, said process comprising mixing a polyamine having three or more amino nitrogen atoms with a feedstock solution comprising the chloride complex of the desired platinum group metal or metals in oxidation state III, in the presence of a protonating agent for the polyamine, and recovering the precipitate. If a desired platinum group metal (Rh, Ir, Ru, Os) is not in oxidation state III, then the metal compound or salt must be converted into the necessary oxidation state III. This may be done by methods well known in the art, generally by reduction. It is, of course, possible to manipulate the oxidation states of a mixture of platinum group metals, so that some are in oxidation state III, and their chloride complexes may be recovered by precipitation, and some are in oxidation state IV, and remain in solution after the treatment with the polyamine.

The invention also provides the salt of the chloride of a said platinum group metal in oxidation state III with a polyamine having three or more amino nitrogen atoms.

The invention further provides the use of a polyamine having three or more amino nitrogen atoms, as a precipitation reagent for the precipitation of rhodium and/or the other said PGM's, in oxidation state III.

Hereinafter, the invention will be particularly described with reference to the refining of rhodium, but it is to be understood that it may also be applied in similar manner to the refining of said other platinum group metals, Ir, Ru and Os.

The feedstock solution may be from any source, and is conveniently a refinery liquor. Such liquors may contain Rh in amounts of about 1% by wt or less, up to about 10% in some circumstances, in combination with one or more other PGM's. Other common components of such liquors include Ni, Co, As, Pb, Cu, Na, Ca, Mg, Ag and Au. Frequently, refinery liquors are chloride solutions and these are particularly acceptable as feedstocks. Otherwise, chloride ions should be added in order to form the required chloride complex, and it is especially preferred to have a chloride present in a concentration of 5 to 6M, in order to maximise the proportion of hexachlororhodate(III) anion. Chloride is preferably present in the form of hydrochloric acid, but may be present or added in the form of a soluble chloride such as NaCl or LiCl.

If the feedstock comprises a hydrochloric acid, this acts as a protonating agent. Otherwise, acids including sulphuric, nitric, phosphoric and hydrochloric acids, may be added to the feedstock.

The most desired feedstocks are chloride refinery liquors from which the major proportion of PGM's, other than rhodium, have been removed by conventional means. That is, such feedstocks contain rhodium as the major component of the PGM content, together with other components which are base metals and may include non-PGM precious metals.

The polyamine reagent is a water-soluble polyamine; this does not require the polyamine to be entirely water-miscible, providing that an adequate amount of the polyamine enters solution under the process conditions to create the desired rhodium salt precipitate. The polyamine may contain primary, secondary and/or tertiary amino groups. Preferred polyamines are those having straight or branched chain hydrocarbon groups, which may be substituted. Suitable polyamines include triethylene tetramine, tetraethylene pentamine, pentaethylene hexamine, aminoethyl piperazine, iminobispropylamine, N-methyl dipropylene triamine and N, N'-dimethyl-N,N'-(bis aminopropyl) ethylene diamine.

The preferred polyamine, however, is diethylene triamine ("DETA"). The polyamine may be added to the feedstock as such, or for handling reasons, it may be preferred to add it as an acid addition salt. Convenient salt forms include the hydrochloride, diacetate, monoacetate, nitrate and sulphate. The polyamine or salt is preferably added to the feedstock in solution in water, the concentration of such solution is not considered to be important, providing that excessive amounts of liquid do not require to be handled. The amount of polyamine added is preferably in excess of the stoichiometric amount, e.g. 1.1–1.8×stoichiometric, when stoichiometry is calculated as with reference to the precipitated salt, $(H_3N^+CH_2CH_2N^+H_2CH_2CH_2N^+H_3)\ [RhCl_6]^{3-}$ for DETA for example. A stoichiometric amount is necessary to precipitate all the rhodium present, but there is a possibility of co-precipitating increasing amounts of palladium in particular, as the amount of polyamine is increased.

The process conditions are not especially critical. It is preferred to stir the feedstock/polyamine mixture at a temperature which may be conveniently ambient but may be up to reflux temperature of approximately 110° C. Preferred temperatures are from 40°–80° C., especially about 60° C. In order to obtain maximum yield, it is preferred to allow the mixture to stand for several hours, for example overnight. It is thought, although we do not wish to be bound by any theory, that such a period permits some rhodium species present to convert into the form required to produce the insoluble precipitate.

The precipitate may be recovered in conventional manner, by filtration, or decantation or centrifugation for example. It is preferred to wash the precipitate, for example with hot HCl, before redissolving the salt in a mixture of concentrated hydrochloric acid and concentrated nitric acid, e.g. in aqua regia. The skilled man will be aware that there is the potential for forming nitrosamines in the presence of nitric acid. The resulting salt solution is then preferably concentrated by evaporation, suitably almost to dryness, and further hydrochloric acid added and these steps are repeated until there is no more evolution of nitrogen oxides, to remove all nitrate residues. The concentrated rhodium salt is then further refined to a desired purity as a compound or rhodium metal sponge, using known techniques, such as are described in the Gmelin Pt Supplement. The method of the invention could, if desired, be used for a further refining step, but economics may favour a more traditional method such as formic acid precipitation or hexanitrito complex salt precipitation.

The present invention will now be described by way of Example only.

EXAMPLE 1

1000 mls of a PGM refinery liquor, containing metals in 6M hydrochloric acid solution, was analysed by Inductively-Coupled Plasma-mass spectroscopy. The results are shown in Table 1 below.

DETA as the hydrochloride, at 1.5 stoichiometric, was dissolved in 158 ml distilled water and added to the stirred liquor feedstock above, at 60° C. A precipitate immediately formed.

After allowing the mixture to cool and stand overnight, the precipitate was filtered off, and washed with 700 ml of hot (50° C.) hydrochloric acid. The washed precipitate was redissolved in aqua regia and analysed in similar way to the feedstock liquor. The results are shown in Table 1, from which it can be seen that the redissolved salt solution contained 99.4% of the Rh contained in the feedstock, and the purity (% Rh by weight) of the salt solution was 99.35% compared to 74% for the feedstock.

TABLE 1

|  | Feedstock (1000 mls) | | Salt Solution (385 ml) | | |
|---|---|---|---|---|---|
|  | ppm | mgms | ppm | mgms | % feed |
| Pt | 34.00 | 34.00 | 11.00 | 4.24 | 12.46 |
| Pd | 879.00 | 879.00 | 17.00 | 6.55 | 0.74 |
| Rh | 15,300.00 | 15,300.00 | 39,500.00 | 15,207.50 | 99.40 |
| Ru | <5.00 | <5.00 | <5.00 | <1.93 | <38.50 |
| Ir | 68.00 | 68.00 | 67.00 | 25.80 | 37.93 |
| Au | <1.00 | <1.00 | 11.00 | 4.24 | 423.50 |
| Ag | 19.00 | 19.00 | 2.00 | 0.77 | 4.05 |
| Os | 0.00 | 0.00 | 0.00 | 0.00 | 0.00 |
| Fe | 14.00 | 14.00 | 17.00 | 8.55 | 48.75 |
| Ni | 2,020.00 | 2,020.00 | 8.00 | 2.31 | 0.11 |
| Cu | 719.00 | 719.00 | 7.00 | 2.70 | 0.37 |
| Co | 49.00 | 49.00 | 1.00 | 0.39 | 0.79 |
| Te | <10.00 | <10.00 | 12.00 | 4.62 | 46.20 |
| Se | <25.00 | <25.00 | <25.00 | <9.63 | <38.50 |
| Pb | 28.00 | 28.00 | 8.00 | 3.08 | 11.00 |
| Ca | 327.00 | 327.00 | 19.00 | 7.32 | 2.24 |
| Al | 43.00 | 43.00 | 4.00 | 1.54 | 3.58 |
| Zn | 8.00 | 8.00 | <1.00 | <0.39 | <4.81 |
| Sb | <9.00 | <9.00 | <9.00 | <3.47 | <38.50 |
| Sn | <4.00 | <4.00 | <4.00 | <1.54 | <38.50 |
| Si | <3.00 | <3.00 | <3.00 | <1.16 | <38.50 |
| As | 1,080.00 | 1,080.00 | 8.00 | 2.31 | 0.21 |
| Bi | 31.00 | 31.00 | <25.00 | <9.63 | <31.05 |
|  | Total | <20,676.00 | Total | <15,307.60 |  |
|  | % Rh | >74.00 | % Rh | >99.35 |  |
|  | % Other PGM | >4.77 | % Other PGM | <0.35 |  |

EXAMPLE 2

The procedure of Example 1 was followed with a 100 mls of the same metal solution. Instead of DETA hydrochloride, however, DETA diacetate was used, at the same stoichiometric ratio. The results are shown in Table 2 below. Although the analysis shows a result for Rh transfer from feedstock to salt solution that is clearly too high for both Rh and Au, it can be concluded that a very high proportion of the Rh is successfully recovered in the salt solution. The analysis figures give a Rh purity of 98.54% compared to 73.93% for the feedstock.

TABLE 2

|  | Feedstock (100 mls) | | Salt Solution (83 ml) | | |
|---|---|---|---|---|---|
|  | ppm | mgms | ppm | mgms | % feed |
| Pt | 34.00 | 3.40 | 8.00 | 0.66 | 19.53 |
| Pd | 879.00 | 87.90 | 34.00 | 3.13 | 3.56 |
| Rh | 15,300.00 | 1,530.00 | 18,300.00 | 1,683.60 | 110.04 |
| Ru | 5.00 | 0.50 | 5.00 | 0.46 | 92.00 |
| Ir | 68.00 | 6.80 | 40.00 | 3.68 | 54.12 |
| Au | 1.00 | 0.10 | 10.00 | 0.92 | 920.00 |
| Ag | 19.00 | 1.90 | 2.00 | 0.18 | 9.68 |
| Os | 0.00 | 0.00 | 0.00 | 0.00 | 0.00 |
| Fe | 14.00 | 1.40 | 12.00 | 1.10 | 78.86 |
| Ni | 2,020.00 | 202.00 | 14.00 | 1.29 | 0.64 |
| Cu | 719.00 | 71.90 | 0.00 | 0.00 | 0.00 |
| Co | 49.00 | 4.90 | 1.00 | 0.09 | 1.88 |
| Te | 10.00 | 1.00 | 10.00 | 0.92 | 92.00 |
| Se | 25.00 | 2.50 | 25.00 | 2.30 | 92.00 |
| Pb | 28.00 | 2.80 | 5.00 | 0.46 | 10.40 |
| Ca | 327.00 | 32.70 | 43.00 | 3.96 | 12.10 |
| Al | 43.00 | 4.30 | 4.00 | 0.37 | 8.56 |
| Zn | 8.00 | 0.80 | 6.00 | 0.55 | 69.00 |
| Sb | 9.00 | 0.90 | 9.00 | 0.83 | 92.00 |
| Sn | 4.00 | 0.40 | 4.00 | 0.37 | 92.00 |
| Si | 3.00 | 0.30 | 3.00 | 0.28 | 92.00 |
| As | 1,080.00 | 108.00 | 11.00 | 1.01 | 0.94 |
| Bi | 31.00 | 3.10 | 25.00 | 2.30 | 74.19 |
|  |  |  | Total | 1,708.46 |  |

TABLE 2-continued

| Feedstock (100 mls) | | Salt Solution (83 ml) | | |
|---|---|---|---|---|
| ppm | mgms | ppm | mgms | % feed |
| | | % Rh | 98.64 | |
| | | % Other PGM | 0.46 | |

EXAMPLE 3

The method of Example 1 was followed, except that 100 mls of a different refinery stream was used, which contained high proportions of Pt, Pd and Ru as well as Rh. The feedstock was also high in Fe, Ni, Cu, Sb, As, Au and Ir. 93.27% of the Rh was recovered, showing especially good selectivity compared to Pt, Pd and the base metals. The results are shown in Table 3 below.

TABLE 3

| | Feedstock (100 mls) | | Salt Solution (162 ml) | | |
|---|---|---|---|---|---|
| | ppm | mgms | ppm | mgms | % feed |
| Pt | 37,800.00 | 3,780.00 | 1,220.00 | 197.64 | 5.23 |
| Pd | 31,000.00 | 3,100.00 | 84.00 | 13.61 | 0.44 |
| Rh | 13,600.00 | 1,360.00 | 7,830.00 | 1,268.48 | 93.27 |
| Ru | 10,900.00 | 1,090.00 | 3,560.00 | 576.72 | 52.91 |
| Ir | 3,680.00 | 368.00 | 1,330.00 | 215.46 | 58.55 |
| Au | 2,910.00 | 291.00 | 1,350.00 | 218.70 | 75.15 |
| Ag | 972.00 | 97.20 | 30.00 | 4.86 | 5.00 |
| Os | 35.00 | 3.50 | 0.00 | 0.00 | 0.00 |
| Fe | 12,100.00 | 1,210.00 | 41.00 | 6.64 | 0.55 |
| Ni | 1,680.00 | 168.00 | 8.00 | 1.30 | 0.77 |
| Cu | 5,380.00 | 538.00 | 10.00 | 1.62 | 0.30 |
| Co | 41.00 | 4.10 | 1.00 | 0.16 | 3.95 |
| Te | 205.00 | 20.50 | 10.00 | 1.62 | 7.90 |
| Se | 837.00 | 83.70 | 25.00 | 4.05 | 4.84 |
| Pb | 341.00 | 34.10 | 16.00 | 2.59 | 7.60 |
| Ca | 402.00 | 40.20 | 1.00 | 0.16 | 0.40 |
| Al | 34.00 | 3.40 | 3.00 | 0.49 | 14.29 |
| Zn | 13.00 | 1.30 | 1.00 | 0.16 | 12.46 |
| Sb | 1,130.00 | 113.00 | 9.00 | 1.46 | 1.29 |
| Sn | 879.00 | 87.90 | 4.00 | 0.65 | 0.74 |
| Si | 5.00 | 0.50 | 3.00 | 0.49 | 97.20 |
| As | 5,380.00 | 538.00 | 8.00 | 1.30 | 0.24 |
| Bi | 117.00 | 11.70 | 25.00 | 4.05 | 34.62 |
| | | | Total | 2,522.18 | |
| | | | % Rh & Tr | | 58.83 |

TABLE 3-continued

| Feedstock (100 mls) | | Salt Solution (162 ml) | | |
|---|---|---|---|---|
| ppm | mgms | ppm | mgms | % feed |
| | | % Other PGM | 31.24 | |

In initial subjective comparative tests carried out using ethylenediamine, hydrazine and DETA, the latter showed a clear advantage in most circumstances, especially as regards selectivity.

Modifications to the invention as particularly described above will be obvious to the skilled man and fall within the general ambit of the invention.

What we claim is:

1. A method for the precipitation of at least one of the platinum group metals consisting of rhodium, iridium, ruthenium, osmium, and mixtures thereof from a feedstock solution, said process comprising mixing a polyamine having three or more amino nitrogen atoms with a feedstock solution comprising a chloride complex of the desired platinum group metal or metals in oxidation state III, in the presence of a protonating agent for the polyamine, and recovering a precipitate.

2. A method as claimed in claim 1, including the preliminary step of converting the platinum group metal or metals that it is desired to precipitate, into oxidation state III.

3. A method as claimed in claim 1, wherein the feedstock solution contains hydrochloric acid, which acts as a source of chloride for said complex and as said protonating agent.

4. A method as claimed in claim 1, wherein the polyamine is used in the form of an acid addition salt.

5. A method as claimed in claim 1, wherein the polyamine contains straight or branched chain hydrocarbon groups.

6. A method as claimed in claim 4, wherein the polyamine is diethylenetriamine.

7. A method as claimed in claim 1, carried out at a temperature of from 40° to 80° C.

8. A method as claimed in claim 1, wherein the amount of polyamine used is in the range 1.1 to 1.8 times stoichiometric.

9. A method as claimed in claim 1, comprising allowing the mixture to stand for several hours before recovering the precipitate.

* * * * *